United States Patent [19]

Perron et al.

[11] Patent Number: 4,951,511
[45] Date of Patent: Aug. 28, 1990

[54] APPARATUS FOR SAMPLING HETEROGENOUS MATERIAL

[75] Inventors: Donald Perron; Robert G. Metka, both of Rouyn-Noranda, Canada

[73] Assignee: Noranda, Inc., Toronto, Canada

[21] Appl. No.: 384,075

[22] Filed: Jul. 24, 1989

Related U.S. Application Data

[63] Continuation of Ser. No. 201,830, Jun. 2, 1988, abandoned.

[30] Foreign Application Priority Data

Mar. 8, 1988 [CA] Canada .................................. 560777

[51] Int. Cl.$^5$ .............................................. G01N 1/00
[52] U.S. Cl. .................................................. 73/863.56
[58] Field of Search ........................ 73/863.41–863.45, 73/863.51–863.58, 863.61, 863.56

[56] References Cited

U.S. PATENT DOCUMENTS

| | | | |
|---|---|---|---|
| 214,734 | 4/1879 | Waugh | 73/863.56 |
| 888,471 | 5/1908 | Constant | 73/863.56 |
| 2,076,188 | 4/1937 | Thorsten | 73/863.56 |
| 3,380,306 | 4/1968 | Pazandak | 73/863.41 |
| 3,397,582 | 8/1968 | Strand | 73/863.45 |
| 4,817,442 | 4/1989 | Loosemore | 73/863.45 |

FOREIGN PATENT DOCUMENTS 1353605 5/1974 United Kingdom ............. 73/863.56

Primary Examiner—Robert Raevis
Attorney, Agent, or Firm—Fleit, Jacobson, Cohn, Price, Holman & Stern

[57] ABSTRACT

An apparatus for sampling a flow of heterogeneous material falling under gravity comprises a rotating table adapted for rotation about a support column, a plurality of removable sampling passageways of identical aperture size mounted side by side around the periphery of the rotating table and adapted to cut the flow of material and a motor for driving the rotating table at constant velocity. The sampling passageways include deflection- and straight-type passageways and the number of deflection-type with respect to straight-type passageways is proportional to the desired percentage of sample to be retained.

4 Claims, 2 Drawing Sheets

INSIDE DEF.
COMPARTMENT
SHOWN

APPARATUS FOR SAMPLING HETEROGENOUS MATERIAL

This application is a continuation of application Ser. No. 201,830, filed June 2, 1988, now abandoned.

FIELD OF THE INVENTION

This invention relates to an apparatus for sampling heterogeneous material, and more particularly, recycled material such as shredded integrated circuits and electronic components.

BACKGROUND OF THE INVENTION

The basic purpose of sampling is to collect, for further physical testing or laboratory analysis, a manageable mass of material which is representative of the total mass of material from which it was collected. This manageable mass of material is called a "sample". A totally homogeneous material requires the collection of only a single sample in order to determine its characteristics accurately, but a heterogeneous material, such as shredded integrated circuits and electronic components, requires the collection of many small samples, or increments, which, when combined, will represent the total mass, or lot, with an acceptable degree of accuracy. These increments should, therefore, be collected from all parts of the lot. The most commonly used apparatus for sampling heterogeneous material are the diverter type cutters. With these samplers, the material being sampled falls by gravity from the end of an overhead conveyor into a diverter which is moved back and forth across the flow of material. In using this type of equipment, some of the particles being sampled invariably fall on the edges of the diverter and are lost, resulting in a sample which is not a true representation of the total mass of the original lot.

SUMMARY OF THE INVENTION

It is, therefore, the object of the present invention to provide a sampler wherein all the particles have the same chance of being included in the sample.

The apparatus, in accordance with the present invention, comprises a rotating table adapted for rotation about a support column, a plurality of removable sampling passageways of identical aperture size mounted side by side around the periphery of the rotating table for receiving the flow of material falling under gravity, and means for driving the rotating table at constant velocity. Some of the sampling passageways are deflection-type passageways and the remaining, straight-type passageways, the number of deflection-type with respect to straight-type passageways being set according to the desired percentage of sample retained with respect to the total flow.

Since all the passageways have identical aperture size and are side by side around the periphery of a rotating table moving at a constant velocity, each of the particles of the flow has an equal chance of passing through a deflection- or a straight-type passageway.

The deflection-type passageways can direct the flow either to the inside or to the outside with respect to the center of the rotating table and when both types of deflector are used, together duplicate samples can be taken simultaneously.

The above-disclosed double-sampling technique also allows one sample to be used for analysis, while the other may be kept as a reference sample without any additional manipulating step and without any risk of segregation.

The interchangeable passageways also offer a wide selection of sampling percentages ranging, for example, from 2.5%, using one deflection-type passageway out of 40 sampling passageways, to 50%, using 20 deflection-type passageways out of 40 sampling passageways.

BRIEF DESCRIPTION OF THE DRAWINGS

The invention will now be disclosed, by way of example, with reference to a preferred embodiment illustrated in the accompanying drawings in which.

DETAILED DESCRIPTION OF THE PREFERRED EMBODIMENTS

Figure 1:
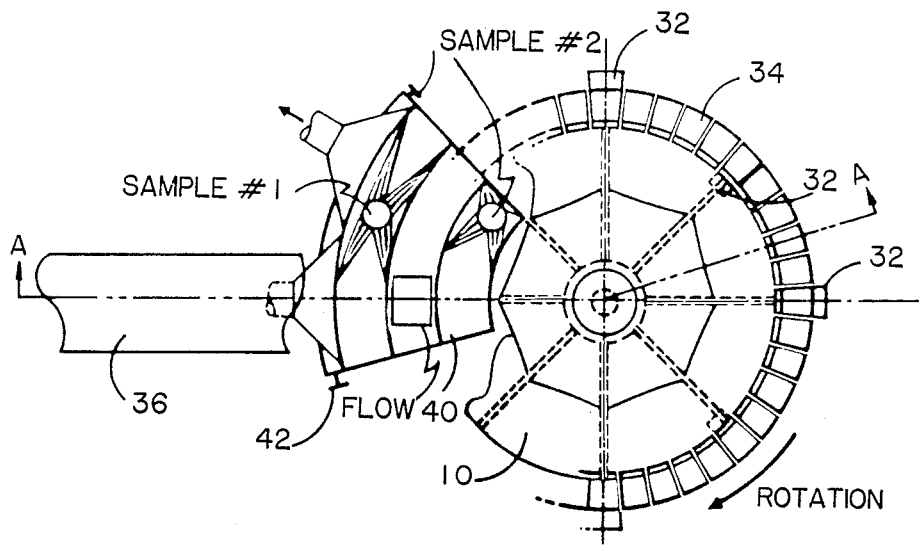
FIG. 1 is a plan view of the sampler in accordance with the present invention.
Figure 2:
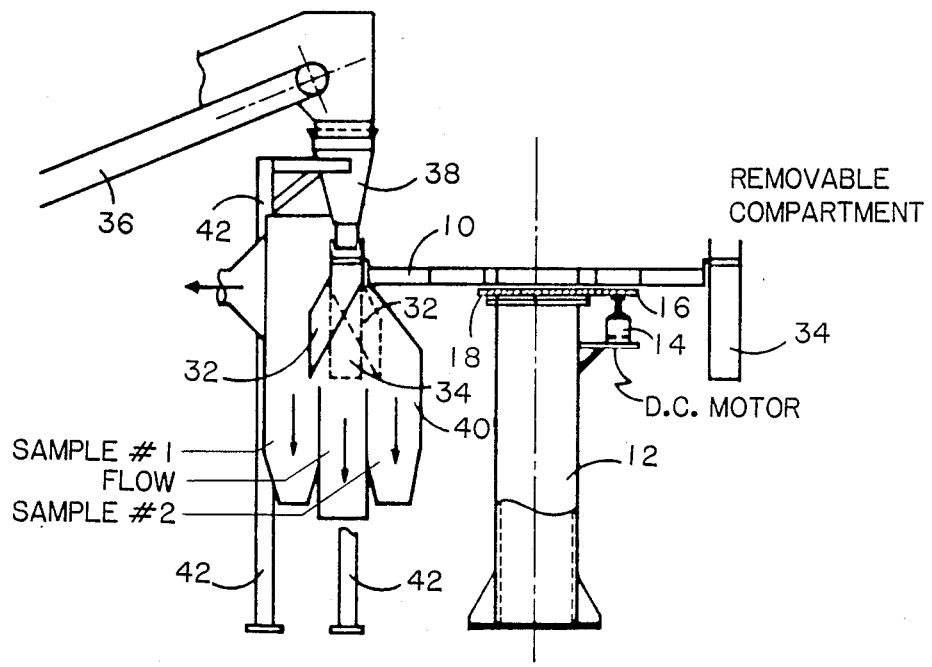
FIG. 2 is a sectional view taken along line A—A of FIG. 1.

Referring to FIGS. 1 and 2, there is shown a sampler comprising a rotating table 10 mounted for rotation through suitable bearings (not shown) about a support column 12. The table is driven at a constant velocity by a variable speed D.C. motor 14 through a pinion 16 connected to the shaft of the motor and engaging a gear 18 secured to the table.

Figure 3:
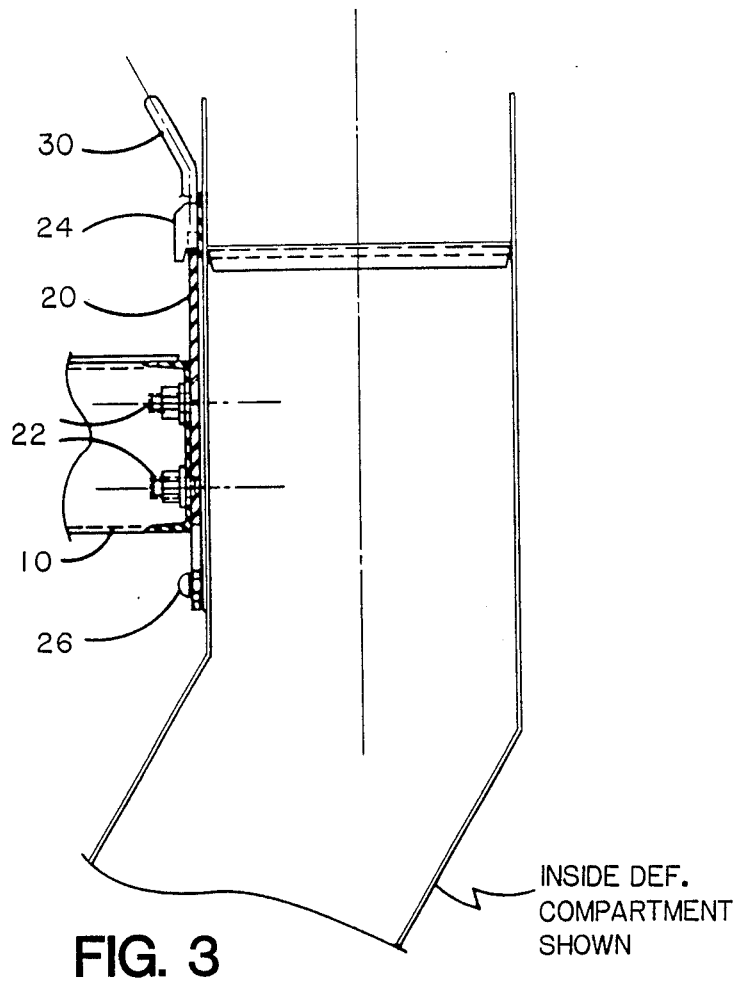
FIGS. 3 and 4 are enlarged views of a typical sampling passageway.
Figure 4:
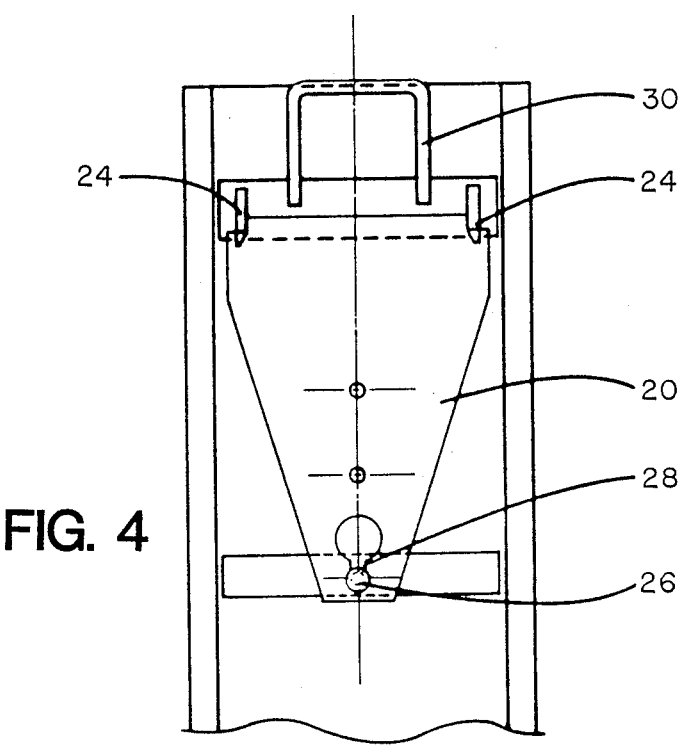

A plurality of removable sampling passageways of identical aperture size are mounted side by side around the periphery of the rotating table 10. The aperture cross-sectional area of the sampling passageways is at least three times the cross-sectional area of the largest particles of material being sampled. As shown in FIGS. 3 and 4, a plurality of mounting plates 20, one for each passageway, are secured to the edge of the rotating table by means of studs 22. Each passageway is provided with a pair of upper hooks 24 which engage the top of the mounting plate, and with a rivet 26 which is engaged in a slot 28 in the bottom of the mounting plate. The passageways may be removed by pulling on a handle 30 provided on the upper part thereof.

The sampling passageways may be of the deflection type, as shown at 32, or of the straight type, as shown at 34. The number of deflection-type passageways with respect to the straight-type passageways depends on the percentage of sample retained with respect to the total flow. Both inside and outside deflection passageways can be used at the same time to allow the simultaneous collection of two samples which may be used, one for analysis, the other as a reference.

The material being sampled goes up a conveyor belt 36 and falls under gravity into an inlet chute 38 which directs the material into the sampling passageways. Since the sampling passageways are in close spaced relationship around the rotating table, all the particles being sampled have the same chance of falling into one or the other passageways and none are lost even if they fall on the edges of the passageways.

The material passes through the respective sampling passageways and falls through a discharge chute 40 which is provided with three sections, one for a sample No. 1 which may be called a reference sample, one for a sample No. 2 which may be called an analysis sample, and a third one for flow through. The inlet and discharge chutes are supported on adequate supporting legs 42.

The material passing through the respective sections of the discharge chute fall into separate receptacles for further handling.

The use of a variable speed D.C. motor allows accurate control of the velocity of the rotating table. For a very heterogeneous material, it is possible to increase the velocity of the table so as to increase the cutting rate of the flow of material to optimize the quality of the samples being taken. The optimum velocity for a particular type of material may be determined by experimentation.

Although the invention has been disclosed with reference to a preferred embodiment, it is to be understood that it is for illustration only and that other alternatives are envisaged within the scope of the following claims.

We claim:

1. A system for sampling a flow of heterogenous material falling under gravity comprising:
   (a) a rotating table adapted for rotation about a vertical support column;
   (b) a plurality of removable sampling passageways of identical aperture size mounted side by side around the periphery of said rotating table and adapted to cut the flow of material, said sampling passageways including deflection-type passageways for sample collection and straight-type passageways for flow through, the number of deflection-type passageways with respect to the total number of passageways being proportional to the desired percentage of the sample to be retained, and said sampling passageways including an equal number of outside and inside deflection-type passageways which deflect material away and towards the center of the rotating table so as to allow simultaneous collection of duplicate samples;
   (c) means for driving said rotating table at constant velocity;
   (d) an inlet chute mounted on a fixed structure for receiving the material to be sampled and having a bottom opening located immediately above the sampling passageways for allowing a flow of said material to fall directly into the sampling passageways as they move under the bottom opening of the inlet chute so as to form a closed system for preventing loss of heterogeneous material made up of shredded integrated circuits and electronic components as they are conveyed by said inlet chute directly into said sampling passageways; and
   (e) a discharge chute also mounted on said fixed structure and having three sections through which flows the material passing through the sampling passageways, one section for each sample being collected and a third section for flow through whereby, all of the material flowing from each of the passageways respectively passes to each of the sections.

2. A system as defined in claim 1, wherein the aperture cross-sectional area of the sampling passageways is at least three times the cross-sectional area of the largest particles of material being sampled.

3. A system as defined in claim 1, wherein said driving means is a variable speed D.C. motor allowing control of the velocity as a function of the flow rate and type of material to be sampled.

4. A system as defined in claim 1, wherein one of the duplicate samples is used for analysis and other as a reference.

* * * * *